United States Patent [19]

Horrobin et al.

[11] Patent Number: 5,603,959

[45] Date of Patent: Feb. 18, 1997

[54] FATTY ACID DERIVATIVES

[75] Inventors: David F. Horrobin, Guildford; Philip Knowles, Carlisle, both of England

[73] Assignee: Scotia Holdings Plc, England

[21] Appl. No.: 392,628

[22] Filed: Feb. 22, 1995

[30] Foreign Application Priority Data

Mar. 1, 1994 [GB] United Kingdom ............. 9403857

[51] Int. Cl.$^6$ ................................. A61K 9/14
[52] U.S. Cl. ............................ 424/490; 424/489
[58] Field of Search ..................... 424/489, 490, 424/184.1, 491

[56] References Cited

U.S. PATENT DOCUMENTS

| | | | |
|---|---|---|---|
| 4,666,701 | 5/1987 | Horrobin et al. | 424/10 |
| 5,043,167 | 8/1991 | Rotini et al. | 424/490 |
| 5,399,347 | 3/1995 | Trentham et al. | 424/184.1 |
| 5,401,516 | 3/1995 | Milstein et al. | 424/491 |

FOREIGN PATENT DOCUMENTS

| | | |
|---|---|---|
| 0062000 | of 1982 | European Pat. Off. . |
| 1594628 | 12/1976 | United Kingdom . |
| 2104513 | 7/1981 | United Kingdom . |

OTHER PUBLICATIONS

Adv. Prostaglandin Thromboxane Res., vol. 6, 1980, pp. 19–25; Corey: "Recent studies on the chemical synthesis of eicosanoids."

Stn International, Karlstruhe, File Registry & JP-A-60142941.

WO-A-91 09831 (Nova Pharmaceutical Corporation).

Primary Examiner—Thurman K. Page
Assistant Examiner—W. Benston
Attorney, Agent, or Firm—Nixon & Vanderhye

[57] ABSTRACT

An NSAID in the form of a compound with an essential fatty acid or essential fatty acid alcohol, particularly an NSAID as listed in categories 1 to 9 herein. Further, a method of preparation of a medicament for the treatment including prophylatic treatment of rheumatoid arthritis, osteoarthritis and related disorders; dysmenorrhoea; dementias, including Alzheimer's disease; or any other inflammatory or other conditions specified herein, wherein the said NSAID is used.

15 Claims, 1 Drawing Sheet

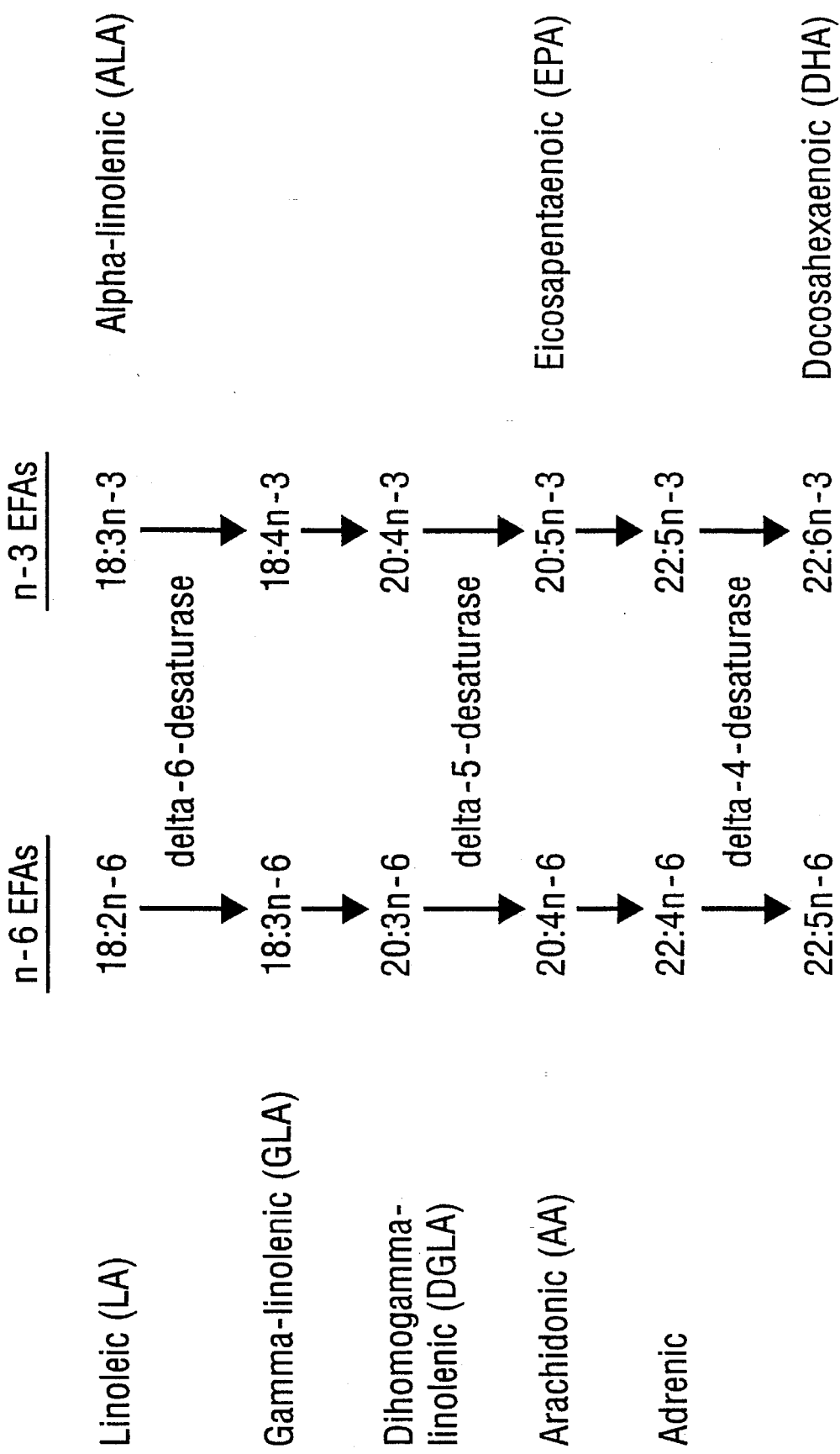

FATTY ACID DERIVATIVES

BACKGROUND

Inflammation is one of the commonest causes of human and animal disability. It plays a major role in diseases such as rheumatoid arthritis, osteoarthritis, gout and ankylosing spondylitis: in reactions to infections of all types, to trauma, and to some cancers; in inflammatory conditions of all organs examples being pancreatitis, myocarditis, dermatitis and pneumonitis; in dysmenorrhoea; and possibly in reactions of blood vessel walls in cardiovascular disease. Recently it has been suggested that dementia also has a major inflammatory component (Rogers J. et al, Neurobiology 43: 1609–1611, 1993). Inflammation is in many situations a normal and desirable response on the part of the body which is directed at bringing a disease process under control. However, in other situations including the various forms of arthritis and the dementias, the inflammation may be excessive and prolonged, so contributing to rather than preventing the damage. In these situations anti-inflammatory drugs may be used to control the inflammation and relieve the symptoms, particularly the pain which can result.

Anti-inflammatory drugs tall into two broad categories, the steroids and the non-steroidal anti-inflammatory drugs (NSAIDs). This specification is concerned with the NSAIDs, many of which act at least in part by blocking the conversion of essential fatty acids (EFAs) to prostaglandins, leukotrienes and other substances generally known as eicosanoids. However, many other facets to the anti-inflammatory and analgesic actions of these drugs have been described and it is unlikely that a single mechanism of action can account for all their effects.

The NSAIDs used as anti-inflammatories and analgesics fall into several broad categories.

1. The salicylates and various derivatives thereof, including acetyl salicylic acid, salicylic acid, methyl salicylate, diflunisal and salsalate.

2. The pyrazolone derivatives, including phenylbutazone, oxyphenbutazone, antipyrine, aminopyrine, dipyrone and apazone.

3. The para-aminophenol derivatives, including acetaminophen (paracetamol), phenacetin and related compounds.

4. Indomethacin, sulindac and related compounds.

5. The fenamates, including; mefenamic, meclofenamic, flufenamic, tolfenamic, and etofenamic acids, and related compounds.

6. The proprionic acid derivatives including ibuprofen, naproxen, fenoprofen, ketoprofen, flurbiprofen and related compounds.

7. The oxicam derivatives such as piroxicam and related compounds.

8. The phenylacetic acid derivatives such as diclofenac and related compounds.

9. Other NSAIDs such as tolmetin, etodolac and nabumetone.

While the NSAIDs have proved extremely valuable in the management of symptoms, they all have two major drawbacks:

1. The control of inflammation is rarely complete and the underlying inflammatory process usually proceeds in spite of drug treatment.

2. All have important side effects, although these vary in severity from drug to drug. The gastro-intestinal tract and the kidneys are particularly likely to be damaged, although adverse effects on almost every tissue have been noted with central nervous system side effects being particularly common with some drugs.

The Invention

We have developed a new drug concept which aims to improve efficacy and reduce side effects. It is based on two facts:

1. There is increasing evidence that essential fatty acids have cytoprotective actions in many situations, but particularly in the gastro-intestinal tract, the kidneys and the brain. Unsaturated essential fatty acids have been shown to prevent or attenuate damage to the stomach, the kidneys and the brain resulting from insults by various drugs, including the NSAIDs. Gammaolinolenic acid is particularly effective in some of these situations.

2. There is also increasing evidence that unsaturated essential fatty acids and especially gamma-linolenic acid (GLA), its immediate derivative within the body, dihomogammalinolenic acid (DGLA), and eicosapentaenoic acid (EPA) have anti-inflammatory actions which are quite different from those of the NSAIDs. Some of these actions are dependent on conversion of the EFAs to anti-inflammatory eicosanoids such as $PGE_1$ and 15-OH-DGLA from DGLA or $PGI_3$ from EPA, others on the unchanged EFAs.

Based on the above, the invention lies in derivatives of the NSAIDs particularly with GLA, DGLA, EPA but also with any of the other EFAs shown in FIG. 1. These derivatives have reduced side effects, increased therapeutic effects, improved formulation characteristics allowing them to be formulated in lipids and made up into soft gelatin capsules, and possibly also improved pharmacokinetic properties with at least partial absorption into the lymphatic system so allowing the liver to be by-passed and also easier passage across barriers to hydrophilic molecules such as cell membranes and the blood-brain barrier.

Any one of the class of NSAIDs can be prepared in the form of a derivative of any of the EFAs, but particularly a derivative of GLA, DGLA or EPA. Examples of appropriate synthetic routes are set out below:

1. Pure GLA or other EFAs, their acid halides, their anhydrides and their mixed anhydrides are prepared by available methods.

2. The corresponding alcohols to GLA or other EFAs are prepared, for example as described below for gamma-linolenol (GLAD, or by a similar method using the lower saturated alkyl esters of EFAs. The alkyl groups can contain from 1–6 carbon atoms.

3. The NSAID derivative of GLA or other EFAs or the NSAID derivative of GLA1 or other EFAls (Essential Fatty Alcohols) are prepared as described for salycylic acid, Indomethacin or Ibuprofen.

In all cases, the formation of the ester linkage $RCO_2R'$ where R is either the main body of the NSAID and R' is the main body of an EFAl or R is the main body of the EFA and R' is the main body of the NSAID, if not specifically given below, may be synthesised by the following methods:

a) By reaction of compounds of type R'OH with compounds of the type R(C=O)X, where X=Cl, or Br, or with compounds of the type R(C=O)O(C=O)R, or with compounds of the type R(C=O)O(C=O)OR", where R" is an alkyl group containing from 1–4 carbon atoms. The reaction is carried out in a suitable solvent, e.g. dichloromethane, in the presence of a tertiary organic base, e.g. pyridine or methylamine, at a temperature between 0°–50° C.

b) By the reaction of compounds of type R(C=O)OH and R'OH in the presence of a condensing agent, e.g. dicyclohexylcarbodiimide, and a strong non-nucleophilic tertiary organic base, e.g. 4-dimethylaminopyfidine, at a temperature between 0°–50° C.

c) By the reaction of compounds of type R(C=O)OH and R'OH in the presence of a suitable enzyme, i.e. a lipase, in a suitable solvent, e.g. hexane at a temperature between 20°–80° C.

In some cases the following reaction conditions apply:

d) By the reaction of compounds of type R(C=O)OH and R'OH in a suitable solvent, e.g. toluene or xylene in the presence of a catalytic amount of mineral or other acid, e.g. p-toluenesulphonic acid, at temperatures between 100°–150° C. with removal of water.

The linkages will usually be ester linkages, fatty-acyl to drug hydroxy as for example in salicylic acid, or fatty-alcohol to drug carboxyl as for example in indomethacin ibuprofen or sulindac. Other links are however not-excluded, for example, ether (fatty alcohol to drug hydroxy); amide (fatty acyl to drug amino); or mixed anhydride (fatty acyl to drug carboxyl), all by use of chemistry known in itself. For example, acetyl salicylic acid (aspirin) may be dissolved in pyridine and reacted with the fatty acid, as its acid chloride in toluene. Alternatively acetylsalicyloyl chloride may be dissolved in toluene and pyridine added to produce an acid chloride adduct. The fatty acid, in toluene, is then added and reaction allowed at room temperature, followed by acid extraction with aqueous hydrochloric acid and removal of toluene to give the acetyl salicylic acid— essential fatty acid mixed anhydride. Or amide links may be formed by reaction with the acid chloride, for example:

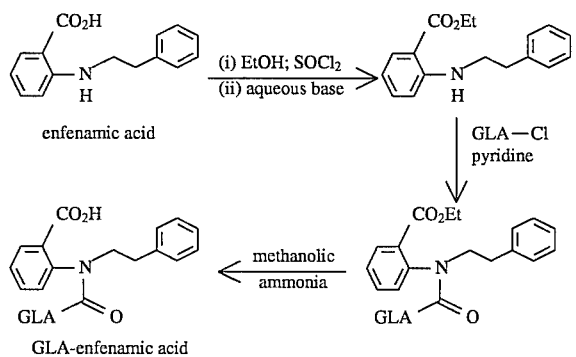

Other such drugs, all in the 11th edition of the Merck index, are enfenamic acid, etofenamate, flufenamic acid, mefenamic acid, tolfenamic acid, diclofenac, parsalmide, amfenac, burnadizon, alminoprofen, benzpiperylon and mesalamine.

The derivatives are generally oils or waxes which enable them to be formulated directly into soft gelatin capsules or to be diluted by other lipids prior to incorporation, or to be prepared in the form of oils, or emulsions for enteral or parenteral application, or as oils, emulsions, creams, lotions, shampoos, sticks, pessaries, powders, microencapsulates or other dosage forms for topical, rectal, vaginal or other local administration.

A particularly desirable type of formulation is to dissolve the oily or waxy NSAIDs derivatives in carrier lipids, such as triglycerides, phospholipids or other appropriate lipids which in themselves deliver high levels of the anti-inflammatory fatty acids, particularly GLA, DGLA and EPA. Such vehicles might include natural oils rich in these fatty acids such as appropriate plant oils containing GLA (e.g. evening primrose, borage, blackcurrant, Astelia, fungal or like oils) or microbial or marine oils containing EPA. They also might include GLA, DGLA or EPA as free acids or as triglycerides containing GLA or EPA and including triglycerides containing 1, 2 or 3 GLA or DGLA moieties or 1, 2 or 3 EPA moieties.

Syntheses

The preparation of gamma-linenol (GLAl) is given, followed by the synthesis of NSAID derivatives.

The Preparation of z,z,z-Octadeca-6,9,12-trienol (gamma-linolenol)

To a suspension of lithium aluminium hydride (50 g) in diethyl ether (1400 ml) under nitrogen was added dropwise with stirring a solution of z,z,z-octadeca-6,9,12-trienoic acid (97%, 200 g) at such a rate that a steady reflux occurred. The mixture was heated under reflux for 4 hours. After cooling to 0°–5° C., water (200 ml) was added cautiously to break down the complex, still maintaining a blanket of nitrogen. To the resulting slurry was added a 10% aqueous solution of sulphuric acid (1500 ml) and a two phase solution occurred. The aqueous layer was separated and the organic layer was washed with water (1000 ml), saturated aqueous sodium bicarbonate (2×1000 ml) and water (2×500 ml). The ether layer was dried ($Na_2SO_4$) and evaporated in vacuo to give a yellow oil. Distillation (148°–150° C./0.06 mmHg) gave z,z,z,-octadeca-6,9,12-trienol (179 g, 94% ) as a colourless oil.

The Preparation of 2-(z,z,z)Octadeca-6,9,12-trienoyl benzoic acid (The GLA derivative of salicylic acid)

Stage 1: 2,2,2-Trichloroethyl salicylate:—A mixture of salicylic acid (90 g), 2,2,2-trichloroethanol (270 g) and concentrated sulphuric acid (50 g) was stirred and heated at 100° C. for 4 hours. The mixture was diluted with chloroform (800 ml) and extracted with water (2×500 ml). After further extraction with saturated aqueous sodium bicarbonate solution (1000 ml), the organic layer was washed with water (2×500 ml) and dried (Mg $SO_4$). The chloroform and excess trichloroethanol was removed in vacuo (65° C./20 mmHg) and the product was distilled (110°–112° C./0.5 mmHg) to give 2,2,2-trichloroethyl salicylate (104 g, 59% ) as a clear liquid which solidified on cooling.

Stage 2: 2,2,2-Trichloroethyl 2-[(z,z,z) octadeca-6,9,12-trienoyl]benzoate:—To a solution of 2,2,2-trichloroethyl salicylate (104 g) in dry pyridine (500 ml) at 0°–5° C. and under nitrogen was added (z,z,z)octadeca-6,9,12-trienoyl chloride (137.5 g) dropwise over a period of one hour. The reaction mixture was allowed to stir for twenty hours at room temperature and then the pyridine was removed in vacuo (25° C./0.5 mmHg). The residue was dissolved in diethyl ether (2000 ml) and water (1000 ml) and the resulting two phase system was shaken and acidified slowly to pH1 by addition of 2M hydrochloric acid. The diethyl ether layer was separated and washed with water (4×1000 ml), adding sodium chloride to break any emulsion that formed. After drying the organic layer ($Na_2SO_4$), the solvent was removed in vacuo to give an orange/brown oil. This was subjected to MPLC (Column size: 15 cm dia.×40 cm, Column packing: Matrex silica, pore size 60A, particle size 35–70 μm, Solvent: initially hexane, then 15% diethyl ether in hexane, Fraction size: 1000 ml). The requisite fractions were evaporated in vacuo to give 2,2,2-trichloroethyl-2-[(z, z,z) octadeca-6,9,12-trienoyl]benzoate. (189 g, 93% yield) as a pale yellow oil.

Stage 3: 2-[(z,z,z) Octadeca-6,9,12-trienoyl]benzoic acid:—2,2,2-Trichloroethyl-2-[(z,z,z) octadeca-6,9,12-trienoyl]benzoate (15 1 g) was dissolved in a mixture of tetrahydrofuran (750 ml), acetic acid (675 ml) and water (75 ml). Zinc dust (150 g) was added. The mixture was stirred at room temperature under nitrogen for 1.5 hours and then allowed to stand for twenty hours. Excess zinc and zinc salts were filtered off through Celite washing the filter pad with tetrahydrofuran (100 ml) and the flitrate was evaporated at 25° C./10 mmHg to remove the tetrahydrofuran. The acetic acid and water was then removed at 25° C./0.5 mmHg. Higher temperatures tend to decompose the product. The resulting oil was dissolved in diethyl ether (1000 ml) and the resulting solution was washed with water (4×200 ml). After drying ($Na_2SO_4$), the ether was evaporated (25° C./10 mmHg) to give a pale yellow oil which was subjected to a dry column (Packing: Matrex silica (1 Kg), pore size 60A, particle size 35–70μm, Fraction size: 1000 ml). The requisite tractions were collected, the solvent evaporated as before, the last traces being removed at 25° C./0.1 mmHg to give 2-[(z,z,z) octadeca-6,9,12,-trienoyl]benzoic acid, (77.8 g, 68%) as a pale orange oil which solidified to a wax in the refrigerator.

The Preparation of z,z,z-Octadeca-6,9,12-trienyl 1-(4-chlorobenzoyl)-5-methoxy-2-methyl indole-3-acetate ("Indomethacin" derivative of gamma-linolenol)

A solution of 1-(4-chlorobenzoyl)-5-methoxy-2-methyl indole-3-acetic acid (Indomethacin, 50.4 g) and thionyl chloride (33.3 g) in 1,2 dichloroethane (700 ml) was heated at 90° C. under nitrogen for four hours. The solvent was removed in vacuo and further portions of dichloroethane (2×200 ml) were added and evaporated to remove the last traces of thionyl chloride. The dark solid residue was dissolved in dichloromethane (700 ml), pyridine (11.7 g) was added and finally z,z,z-octadeca-6,9,12-trienol (35.4 g). The mixture was stirred under nitrogen at room temperature for forty eight hours. Due to emulsion formation, the solvent was then removed and replaced with ethyl acetate (1000 ml), the organic layer being washed successively with brine (500 ml), 2M hydrochloric acid (500 ml), brine (500 ml), saturated aqueous sodium bicarbonate (500 ml) and water (2×500 ml). After drying ($Na_2SO_4$) the solvent was evaporated to give a yellow oil which was subjected to MPLC (Column size: 150mm dia.×300 mm. Column packing: Matrex silica, pore size 60A, particle size 35–701μm, Solvent: 5 % ethyl acetate in hexane, Fraction size: 2000 ml). The requisite fractions were collected and evaporated (50° C./20 mmHg then 70° C./0.1 mmHg) to give z,z,z-octadeca-6,9,12-trienoyl 1-(4-chlorobenzoyl)-5-methoxy-2-methyl indole-3-acetate. (55.5 g, 68 % ) as a yellow oil.

The Preparation of z,z,z-octadeca-6,9,12-trienyl 2-methyl-4'(2-methyl propyl)-phenylacetate ("Ibuprofen" derivative of gamma-linolenol)

A solution of 2-methyl-4'-(2-methylpropyl) phenylacetic acid (Ibuprofen) (1.14 g), z,z,z-octadeca-6,9,12-trienol (1.32 g), 4-dimethylaminopyridine (0.61 g) and dicyclohexylcarbodiimide (1.13 g) in dichloromethane (20 ml) was stirred at room temperature under nitrogen for 20 hours. The mixture was filtered and washed with 2M hydrochloric acid (50 ml), water (50 ml), saturated aqueous sodium bicarbonate (2×50 ml) and finally water (2×50 ml). After drying ($Na_2SO_4$), the solvent was evaporated in vacuo and the residue was subjected to chromatography using a dry column (packing: Matrex silica, pore size 60A, particle size 35–70μm, (100 g); solvent: 20% ethyl acetate in hexane). The requisite fractions were collected and evaporated (50° C./20 mmHg and then 50° C./0.05 mmHg/3 h) to give z,z,z-octadeca-6,9,12-trienyl 2-methyl 4'-(2-methylpropyl) phenylacetate (1.76 g, 70%) as a pale yellow oil.

The Preparation of GLA alcohol ester of (Z)-5-fluoro-2-methyl-1-[[4-(methylsulfinyl) phenyl]methylene]-1H-indene-3-acetic acid ("Sulindac" derivative of gamma-linolenol)

A solution of 1,3-dicyclohexylcarbodiimide (750 mg; 3.6 mmol) and 4-(N,N-dimethylamino) pyridine (390 mg; 3.2 mmol) in dichloromethane (10 ml) was added to a solution of sulindac (1 g; 2.8 mmol) and z,z,z-octadeca-6,9,12-trienol (850 mg; 3.03 mmol) in dichloromethane (30 ml) at room temperature. The resulting solution was stirred at room temperature under an atmosphere of nitrogen for 2 hours. The mixture was filtered and the filtered material washed with dichloromethane. The combined filtrates were concentrated and purified by dry column chromatography (100% ethyl acetate) to yield the title compound as a yellow waxy solid.

Possible Uses

These drugs may be used for any purpose for which NSAIDs are currently used and in particular for those purposes outlined in the introduction to the specification. Particularly important uses are rheumatoid arthritis, osteoarthritis, dementias including Alzheimer's disease, and dysmenorrhoea.

Doses

The dose levels for each drug on a molar basis are the same or similar as the molar doses of the parent NSAID compounds and well known in themselves.

EXAMPLES

1. "Indomethacin-gamma-linolenol" (IGL) is formulated into soft gelatin capsules each containing 20 mg, 50 mg or 100 mg of the drug. Encapsulation may be assisted by mixing the drug with an appropriate carrier such as an oil containing free GLA, free DGLA, tree EPA or triglycerides or a phospholipid enriched in GLA, DGLA or EPA such as tri-GLA, tri-EPA, DLMG (di-linoleoyl-mono-gamma-linolenoyl glyceride, LGG, GGE, GEE (L=linoleoyl, G=gammalinolenoyl, E=eicosapentaenoyl) or other triglycerides containing 1, 2 or 3 GLA or DGLA moieties and/or 1, 2 or 3 EPA moieties.

2. IGL formulated for oral or enteral administration as a syrup, emulsion, oil, whip, mousse, micro-encapsulated powder or other appropriate dosage form with or without appropriate flavouring.

3. IGL formulated for parenteral administration as an oil or emulsion.

4. IGL formulated for topical administration as a cream, lotion, ointment, stick, shampoo or other appropriate formulation containing from 0.001% to 50% IGL, preferably 0.01% to 5% and very preferably 0.1% to 2%, by weight.

5-8. As examples 1-4 but with "ibuprofen-gamma-linolenol" (IbGL) as the active material, when in capsules each one containing 250 mg, 500 mg or 750 mg IbGL.

9-12. As examples 1-12 but with "salicyclic acid gamma-linolenate" (AGL) as the active material; when in capsules each one containing 250 mg, 500 mg or 750 mg AGL.

13-24. As examples 1-12 but with the NSAID derivatives made with EPA rather than GLA.

In further examples the NSAID may be any other compound on the list herein.

We claim:

1. An NSAID in the form of a compound in which the NSAID is chemically linked to an n-6 or n-3 essential fatty acid selected from the group consisting of linolenic acid, gamma-linolenic acid, dihomo-gamma-linolenic acid, arachidonic acid, adrenic acid, docosapentaenoic n-6 acid, alpha-linolenic acid, stearidonic acid, the 20:4n-3 acid, eicosapentaenoic acid, docosapentaenoic n-3 acid, docosahexaenoic acid, and the corresponding fatty alcohols, wherein said NSAID is selected from the group consisting of a salicylate, a pyrazolone, a para-aminophenol, indomethacin, sulindac, a fenamate, a propionic acid, an oxicam, a phenylacetic acid, tolmetin, etodolac and nabumetone.

2. An NSAID in the form according to claim 1, wherein said NSAID is selected from the group consisting of acetyl salicylic acid, salicylic acid, methyl salicylate, diflunisal, salsalate, phenylbutazone, oxyphenbutazone, antipyrine, aminopyrine, dipyrone, apozone, acetaminophen, phenacetin, indomethacin, sulindac, mefenamic, meclofenamic, flufenamic, tolfenamic, etofenamic acid, ibuprofen, naproxen, fenoprofen, ketoprofen, flurbiprofen, prioxicam, diclofenac, tolmetin, etodolac and nabumetone.

3. An NSAID in the form according to claim 2, wherein the NSAID is ibuprofen, sulindac or salicylic acid.

4. An NSAID in the form according to claim 3, wherein the NSAID is linked to gamma-linolenic, dihomo-gamma-linolenic acid or eicosapentaenoic acid, or the corresponding fatty alcohols.

5. A composition comprising an NSAID selected from the group consisting of a salicylate, a pyrazole, a para-aminophenol, indomethacin, sulindac, a fenamate, a propionic acid, an oxicam, a phenylacetic acid, tolmetin, etodolac and nabumetone in the form of a compound in which the NSAID is chemically linked to an n-6 or n-3 essential fatty acid selected from the group consisting of linolenic acid, gamma-linolenic acid, dihomo-gamma-linolenic acid, arachidonic acid, adrenic acid, docosapentaenoic n-6 acid, alpha-linolenic acid, stearidonic acid, eicosapentaenoic acid, docosapentaenoic n-3 acid, docosahexaenoic acid, and the corresponding fatty alcohols, together with a free essential fatty acid or an essential fatty acid glyceride or phospholipid, as a carrier.

6. An NSAID in the form according to claim 5, wherein an essential fatty acid in the carrier is gamma-linolenic acid, dihomo-gamma-linolenic acid, eicosapentaenoic acid or mixtures thereof.

7. A method of treating rheumatoid arthritic, osteoarthritic, dysmenorrhea or dementia comprising administering to a person in need of such treatment comprising an NSAID in the form of a compound in which the NSAID is chemically linked to n-6 or n-3 essential fatty acid selected from the group consisting of linoleic acid, gamma-linolenic acid, dihomo-gamma-linolenic acid, arachidonic acid, adrenic acid, docosapentaenoic n-6 acid, alpha-linolenic acid, stearidonic acid, eicosapentaenoic acid, docosapentaenoic n-3 acid, docosahexaenoic acid, and the corresponding fatty alcohols, wherein said NSAID is selected from the group consisting of a salicylate, a pyrazolone, a para-aminophenol, indomethacin, sulindac, a fenamate, a priopionic acid, an oxicam, a phenylacetic acid, tolmetin, etodolac and nabumetone.

8. A method according to claim 7, wherein the NSAID is selected from the group consisting of acetyl salicylic acid, salicylic acid, methyl salicylate, diflunisal, salsalate, phenylbutazone, oxyphenbutazone, antipyrine, aminopyrine, dipyrone, apozone, acetaminophen, phenacetin, indomethacin, sulindac, mefenamic, meclofenamic, flufenamic, tolfenamic, etofenamic acid, ibuprofen, naproxen, fenoprofen, ketoprofen, flurbiprofen, prioxicam, diclofenac, tolmetin, etodolac and nabumetone.

9. A method according to claim 8, wherein the NSAID is ibuprofen, sulindac or salicylic acid.

10. An NSAID in the form according to claim 4, wherein the NSAID is linked to gamma-linolenic, dihomo-gamma-linolenic acid or eicosapentaenoic acid, or the corresponding fatty alcohols.

11. A method of treating rheumatoid arthritis, osteoarthritis, dysmenorrhea or dementia comprising administering to a person in need of such treatment a composition comprising together with a carrier, an NSAID in the form of a compound in which the NSAID is chemically linked to an n-6 or n-3 essential fatty acid selected from the group consisting of linoleic acid, gamma-linolenic acid, dihomo-gamma-linolenic acid, arachidonic acid, adrenic acid, docosapentaenoic n-6 acid, alpha-linolenic acid, stearidonic acid, eicosapentaenoic acid, docosapentaenoic n-3 acid, docosahexaenoic acid, and the corresponding fatty alcohols, wherein said NSAID is selected from the group consisting of salicylate, a pyrazolone, a para-aminophenol, indomethacin, sulindac, a fenamate, a propionic acid, an oxicam, a phenylacetic acid, tolmetin, etodolac and nabumetone in the form of a compound with an n-6 or n-3 essential fatty acid or essential fatty alcohol comprising a salicylate, a pyrazolone, a paraaminophenol, indomethacin, sulindac, a fenamate, a proprionic acid, an oxicam, a phenylacetic acid, tolmetin, etodolac and nabumetone.

12. A method according to claim 11, wherein the NSAID is selected from the group consisting of acetyl salicylic acid, salicylic acid, methyl salicylate, diflunisal, salsalate, phenylbutazone, oxyphenbutazone, antipyrine, aminopyrine, dipyrone, apozone, acetaminophen, phenacetin, indomethacin, sulindac, mefenamic, meclofenamic, flufenamic, tolfenamic, etofenamic acid, ibuprofen, naproxen, fenoprofen, ketoprofen, flurbiprofen, prioxicam, diclofenac, tolmetin, etodolac and nabumetone.

13. A method according to claim 12, wherein the NSAID is ibuprofen, sulindac or salicylic acid.

14. A method according to claim 11, wherein the NSAID is linked to linoleic, gamma-linolenic, dihomo-gamma-linolenic, arachidonic, adrenic, docosapentaenoic n-6, alpha-linoleic, stearidonic, eicosapentaenoic, docosapentaenoic n-3, or docosahexaenoic acid, or the corresponding fatty alcohols.

15. A method according to claim 24, wherein the NSAID is linked to gamma-linolenic, dihomo-gamma-linolenic acid or eicosapentaenoic acid, or the corresponding fatty alcohols.

* * * * *